United States Patent [19]

Coates et al.

[11] 4,111,936

[45] Sep. 5, 1978

[54] PYRIDAZINETHIONES

[75] Inventors: William John Coates, Welwyn Garden City; Anthony Maitland Roe, Hatfield; Robert Antony Slater, Letchworth; Edwin Michael Taylor, Welwyn, all of England

[73] Assignee: Smith Kline & French Laboratories Limited, Welwyn Garden City, England

[21] Appl. No.: 816,986

[22] Filed: Jul. 19, 1977

Related U.S. Application Data

[63] Continuation-in-part of Ser. No. 583,379, Jun. 3, 1975, Pat. No. 4,053,601.

[30] Foreign Application Priority Data

Jun. 18, 1974 [GB] United Kingdom ............... 26864/74
Jan. 2, 1975 [GB] United Kingdom ...................... 20/75

[51] Int. Cl.$^2$ ..................... C07D 237/18; A01N 31/50
[52] U.S. Cl. ..................................... 544/239; 424/250
[58] Field of Search ..................................... 260/250 A

[56] References Cited

U.S. PATENT DOCUMENTS 3,931,177  1/1976  Coates et al. ..................... 260/250 A

OTHER PUBLICATIONS

Castle et al., "The Chemistry of Heterocyclic Cmpds" (Wiley & Sons, 1973), p. 797, p. 834.
Coates et al. II, Chem. Abs. 84, 164819; (1976).

*Primary Examiner*—Donald G. Daus
*Assistant Examiner*—Mark L. Berch
*Attorney, Agent, or Firm*—Joan S. Keps; Richard D. Foggio; William H. Edgerton

[57] ABSTRACT

Substituted phenyl pyridazinethiones which are useful intermediates in the preparation of substituted phenylhydrazinopyridazines which have β-adrenergic blocking and vasodilator activity.

13 Claims, No Drawings

PYRIDAZINETHIONES

This application is a continuation-in-part of Ser. No. 583,379 filed Jun. 3rd 1975 now U.S. Pat. No. 4,053,601.

This invention relates to pharmacologically active compounds and in particular to certain substituted phenyl pyridazinethiones which have β-adrenergic blocking activity and are useful intermediates in the preparation of certain substituted phenyl hydrazinopyridazines which have β-adrenergic blocking and vasodilator activity. This invention also relates to pharmaceutical compositions comprising said substituted phenyl pyridazinethiones and to methods of treatment employing their use.

The compounds of the present invention may be represented by the following Formula I:-

FORMULA 1

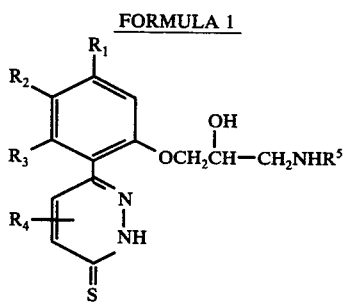

wherein two of the groups $R_1$, $R_2$ and $R_3$ are hydrogen and the third group is hydrogen, lower alkyl, fluoro, chloro, bromo, trifluoromethyl, hydroxy, lower alkoxy, lower alkenyloxy, lower alkoxycarbonyl, cyano, —$CONH_2$, —$CH_2CONH_2$, nitro, amino, lower alkanoylamino, lower alkylamino or di(lower alkyl)amino; $R_4$ is hydrogen or methyl; $R^5$ is isopropyl, tertiary butyl or phenylethyl.

Throughout the specification and claims, by the terms 'lower alkyl', 'lower lkoxy', 'lower alkenyloxy' and 'lower alkanoyl' we mean alkyl, alkoxy, alkenyloxy and alkanoyl groups containing a chain of no more than four carbon atoms, which chain may, where possible, be branched.

In a preferred group, $R_1$, $R_2$ and $R_3$ are all hydrogen, or one of $R_1$, $R_2$ and $R_3$ is methyl, fluoro, chloro, methoxy or cyano. Particularly preferably $R_3$ is hydrogen.

In another preferred group $R_3$ is hydrogen and either $R_1$ or $R_2$ is trifluoromethyl, allyloxy, —$CH_2CONH_2$ or acetamido, particularly preferably —$CH_2CONH_2$ or acetamido. Preferably $R_4$ is hydrogen.

Preferably $R^5$ is isopropyl or tertiary butyl.

Examples of particularly preferred compounds which fall within the scope of the present invention are:
6-[2-(3-t-butylamino-2-hydroxypropoxy)-phenyl]3(2H)-pyridazinethione
6-[2-(3-t-butylamino-2-hydroxypropoxy)-4-methylphenyl]-3(2H)-pyridazinethione
6-[2-(3-t-butylamino-2-hydroxypropoxy)-4-methoxyphenyl]-3(2H)-pyridazinethione
6-[4-acetamido-2-(3-t-butylamino-2-hydroxypropoxy)phenyl]-3(2H)-pyridazinethione The compounds of this invention exist as optical isomers and the S-absolute configuration is preferred. Racemic mixtures of the compounds of Formula 1 can be resolved by conventional methods, such as recrystallization of salts formed with optically active acids.

The compounds of Formula 1 may be prepared by the processes outlined in Scheme 1. In the schemes $R^1$, $R^2$ and $R^3$ have the same significance as in Formula 1 or they may also be protected derivatives thereof or precursors thereof.

SCHEME 1

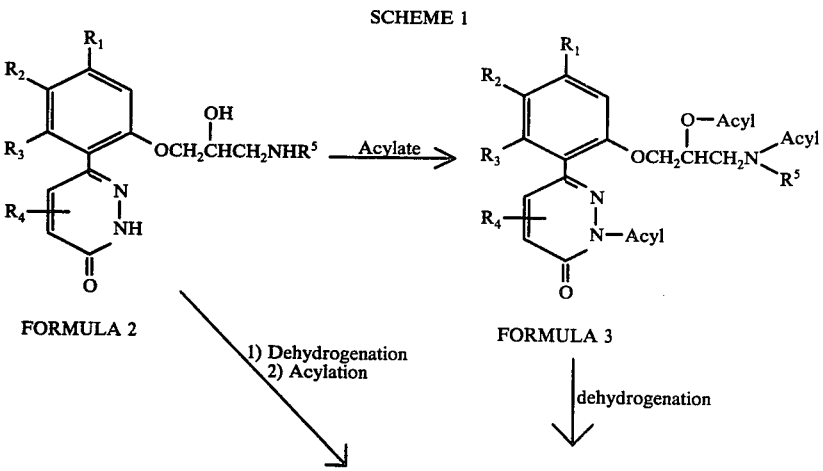

SCHEME 1

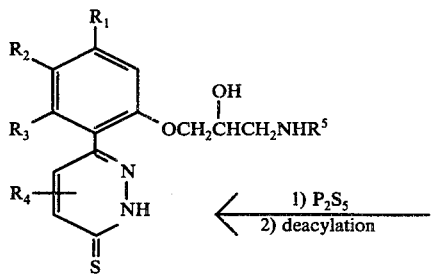

FORMULA 1

-continued

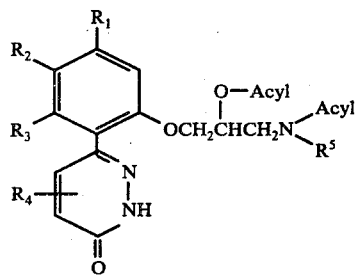

FORMULA 4

Acylation of a phenyl dihydropyridazinone of Formula 2, wherein $R_1$, $R_2$, $R_3$, $R_4$ and $R_5$ have the same significance as in Formula I, gives a compound of Formula 3, wherein the hydroxy and amino groups of the side chain are protected. A suitable acyl group is the acetyl group which may be introduced by reaction of a compound of Formula 2 with acetic anhydride in the presence of a suitable base, e.g., pyridine or potassium acetate. Acetylation of the dihydropyridazinone ring also occurs, and this acetyl group is removed during subsequent bromination. Another suitable acyl group is the benzyloxycarbonyl group which may be introduced by treating a compound of Formula 2 with benzyl chloroformate under basic conditions. The triacylated compound of Formula 3 is dehydrogenated to gave a phenylpyridazinone of Formula 4.

In many cases bromine in acetic acid is a suitable reagent for this dehydrogenation, and when the acyl group is acetyl it is preferred that the compound of Formula 3 is not isolated before treatment with bromine. In cases where the use of bromine is inappropriate, e.g., where the compound of Formula 2 is susceptible to nuclear bromination (i.e. when $R_1$, $R_2$ or $R_3$ is a group such as hydroxy or amino), and when $R_1$, $R_2$ or $R_3$ is sensitive to bromine or hydrogen bromide (e.g. allyloxy), dehydrogenation of a compound of Formula 2 can be achieved by the use of sodium 3-nitrobenzene sulphonate, chloranil or other similar dehydrogenating agents, and is followed by acylation to give a compound of Formula 4. Treatment of the phenylpyridazinone of Formula 4 with phosphorus pentasulphide in pyridine gives the corresponding thione (which may be obtained in mixture with the corresponding N-thioacylaminopropyl derivative) which is deacylated under suitable conditions to give the thiones of Formula 1. The acetyl group may conveniently be removed using sodium hydroxide in methanol.

The compounds of Formula 1 are referred to as thiones and are drawn as such, but these compounds may also exist in a tautomeric mercaptopyridazine form. Similarly the pyridazinones of Formula 4 may exist as a tautomeric mixture with the corresponding hydroxypyridazines. The intermediate phenyl dihydropyridazinones of Formula 2 may be prepared according to a reaction sequence shown in Scheme 2, wherein $R_1$, $R_2$, $R_3$, $R_4$ and $R_5$ have the same significance as in Formula 1 and one of $R^6$ and $R^7$ may be methyl and $R^8$ is hydroxy, amino or any other suitable group such as lower alkoxy or lower alkylamino, which can be displaced with hydrazine.

Many of the phenyldihydropyridazinones of Formula 2 are described in U.S. Pat. No. 3931177.

The compounds of Formula 5 may be produced from the corresponding compounds of Formula 7:

FORMULA 7

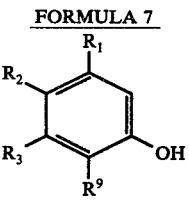

wherein $R_1$, $R_2$ and $R_3$ have the same significance as in Formula 1 and $R^9$ is hydrogen or bromine or —COCH$_2$R$_4$. When $R^9$ is hydrogen, reaction with succinic anhydride and a Lewis acid such as aluminium trichloride may be used. When $R^9$ is bromine, formation of a Grignard reagent with magnesium and subsequent reaction of this with, for example, N-methylsuccinimide provides a useful method, the hydroxyl group being protected during this reaction for example by benzylation.

SCHEME 2
(X represents Chlorine or Bromine)

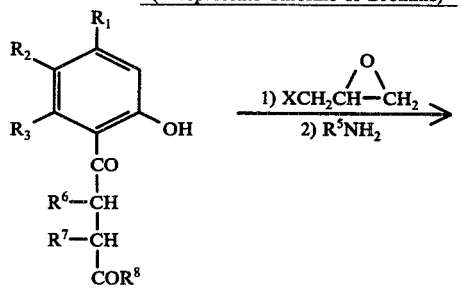

FORMULA 5

-continued
SCHEME 2
(X represents Chlorine or Bromine)

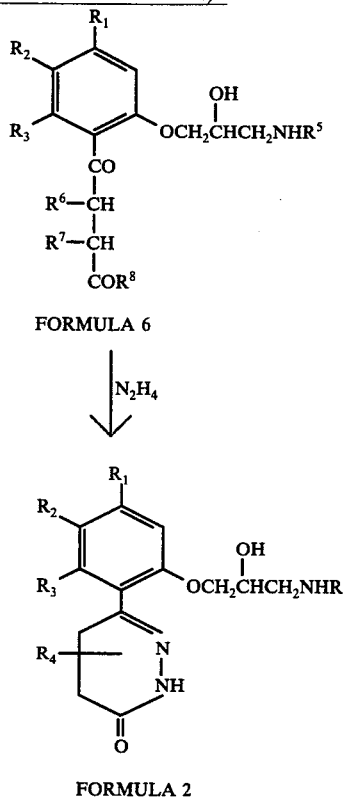

FORMULA 6

FORMULA 2

In each case of course the succinic anhydride or N-methylsuccinimide may be substituted with a methyl group to give the appropriate compounds of Formula 5 wherein either $R^6$ or $R^7$ is methyl. When $R^9$ is —COCH$_2$R$_4$, the phenol of Formula 7 is treated with formaldehyde and a di-(lower alkyl) amine to give a compound of Formula 8 wherein $R^{10}$ is lower alkyl or $(R^{10})_2$ is a polymethylene chain which forms a heterocyclic ring with the nitrogen atom shown. The compounds of Formula 8 may be alkylated to give the corresponding quaternary derivatives. The compounds of Formula 8 and the corresponding quaternary derivatives may be treated with an inorganic cyanide to give a nitrile of Formula 9. The phenol group may be protected, for example as the acetate ester, during the processes.

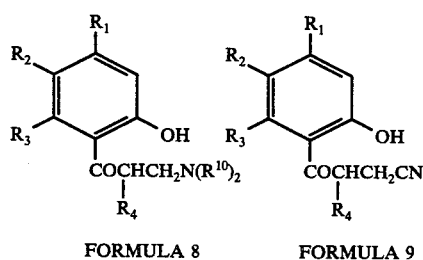

FORMULA 8   FORMULA 9

The compounds of Formula 5 may readily be obtained from the nitriles of Formula 9 e.g., by hydrolysis of the latter to the corresponding amides or carboxylic acids.

The compounds of Formula 5 are successively treated with epichlorohydrin or epibromohydrin, in amine $R^5NH_2$, and hydrazine to give the phenyldihydropyridazinones of Formula 2. Alternatively, the phenyldihydropyridazinones of Formula 2 may be prepared by first treating the compounds of Formula 5 with hydrazine to give the dihydropyridazinones of Formula 9 and successively treating these compounds with epichlorohydrin or epibromohydrin, and then an amine $R^5NH_2$, as shown in Scheme 3. With the latter route alkylation of the dihydropyridazinone ring may occur.

SCHEME 3
(X represents Chlorine or Bromine)

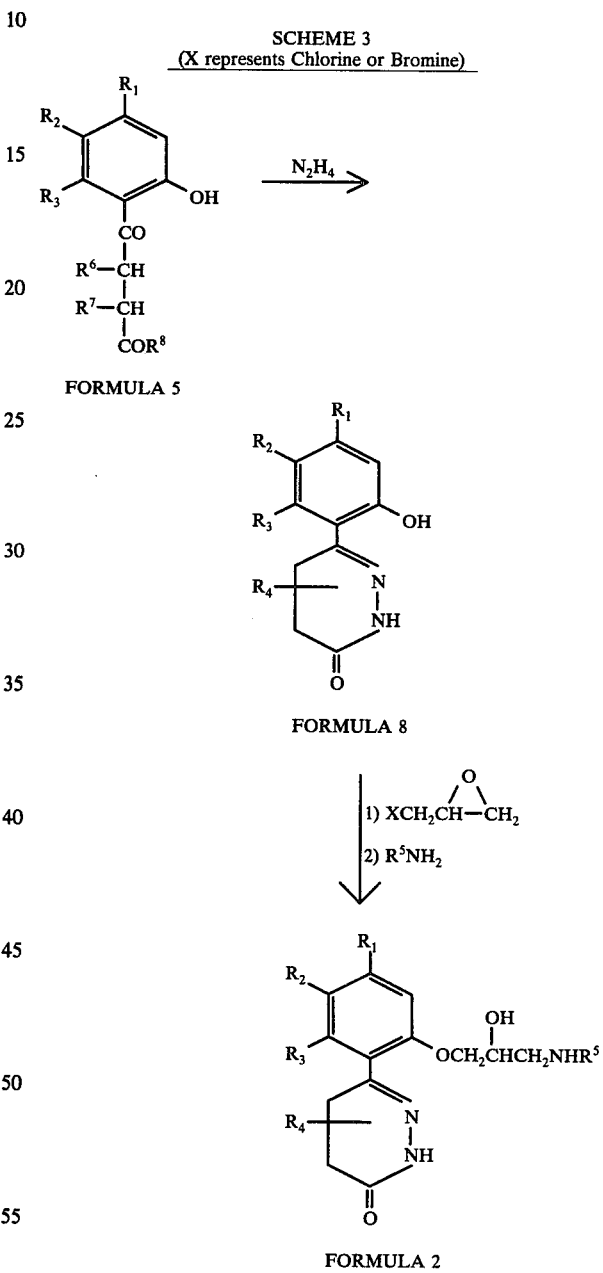

FORMULA 2

In all the series of reactions described the hydrazino group may be introduced by reactions with hydrazine or a protected derivative thereof, such as t-butyl carbazate or a hydrazone of an aldehyde or ketone.

The compounds of Formula 1 are useful as intermediates in the production of hydrazinopyridazine compounds of Formula 10 which are described in our copending U.S. Application Ser. No. 583,379 now U.S. Pat. 4053601 and which have β-adrenergic blocking and vasodilator activity.

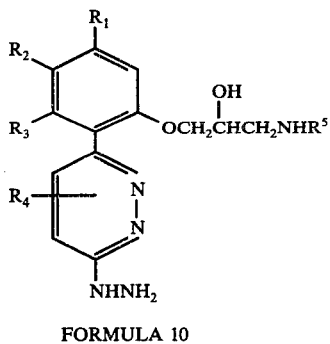

FORMULA 10

In Formula 10, $R_1$, $R_2$, $R_3$, $R_4$ and $R^5$ have the same significance as in Formula 1. Compounds of Formula 10 may be prepared by treating a compound of Formula 1 with hydrazine.

As stated above, the compounds of Formula 1 are β-adrenergic blocking agents. β-Adrenergic blocking agents are useful in the treatment of angina pectoris, cardiac arrhythmias and hypertension. The β-adrenergic blocking activity of our compounds may be demonstrated in a suitable test preparation such as cats anaesthetised with pentobarbitone sodium (Nembutal), 60 mg/Kg i.p. In such anaesthetised cats, intravenous injections of isoprenaline cause tachycardia, and vasodilatation in the hind-limb. These effects of isoprenaline, which are dose-dependent and are due to stimulation of β-adrenoreceptors, can be reduced or abolished by intravenous administration of from 0.01 to 100 micromoles/Kg of the β-adrenergic blocking agent of Formula 1.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric, acetic, citric and maleic acids.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Examplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 500 mg. If a liquid carrier is used, the preparation may be in the form of a syrup, emulsion, soft gelatin capsule, sterile injectable liquid such as in an ampoule, or an aqueous or nonaqueous liquid suspension. The pharmaceutical compositions are prepared by conventional techniques involving procedures such as mixing, granulating and compressing or dissolving the ingredients as appropriate to the desired preparation.

The active ingredient will be present in the composition in an effective amount to produce β-adrenergic blockade. The route of administration may be oral or parenteral.

Preferably, each dosage unit will contain the active ingredient in an amount of from about 25 mg to about 500 mg most preferably from about 50 mg to about 250 mg.

The active ingredient will preferably be administered in equal doses one to three times per day. The daily dosage regimen will preferably be from about 100 mg to about 2 g.

Other pharmacologically active compounds may in certain cases be included in the composition. Advantageously the composition will be made up in a dosage unit form appropriate to the desired mode of administration for example as a tablet, capsule or injectable solution.

The invention is illustrated but in no way limited by the following examples, wherein all temperatures are given in degrees centigrade:

EXAMPLE 1

Preparation of 6-[2-(2-hydroxy-3-isopropylaminopropoxy)phenyl]-3(2H)-pyridazinethione (i) Hydrogen chloride was bubbled into a gently boiling solution of the known 3-(2-hydroxybenzoyl)propionic acid (10 g. 0.05 mole) in dry methanol (20 ml) until esterification was complete. The solution was poured into ice-water and the ester extracted into dichloromethane. The organic solution was washed with water and evaporated to give methyl 3-(2-hydroxybenzoyl)propionate (10.55 g, 98%) as a pale yellow oil.

(ii) A well stirred mixture of methyl 3-(2-hydroxybenzoyl)-propionate (63.3 g, 0.3 mole), potassium carbonate (48.4 g, 0.35 mole), epibromohydrin (117 ml, 1.4 mole), and dry ethyl methyl ketone (2000 ml) was heated under reflux for 28 hours. Evaporation of the filtered solution under reduced pressure gave methyl 3-[2-(2,3-epoxypropoxy)benzoyl]-propionate (83 g, 100%). (Found: $M^+$, 264; $C_{14}H_{16}O_5$ requires M, 264).

(iii) A stirred mixture of methyl 3-[2-(2,3-epoxypropoxy)benzoyl]propionate (8.3 g, 0.031 mole), and isopropylamine (16.4 ml, 0.19 mole) was heated under reflux for 90 minutes. Evaporation of the solution under reduced pressure gave methyl 3-[2-(2-hydroxy-3-isopropylaminopropoxy)benzoyl]-propionate (10.2 g, 100%) as a pale brown oil.

(iv) Hydrazine hydrate (4.65 ml, 0.09 mole) was added to a solution of methyl 3-[2-(2-hydroxy-3-isopropylaminopropoxy)-benzoyl]propionate (10 g, 0.03 mole) in glacial acetic acid (80 ml) and the solution was heated under reflux for one hour. Evaporation under reduced pressure gave an oil (25.5 g) which was dissolved in water, treated with an excess of sodium carbonate solution and extracted with dichloromethane. Evaporation of the dried extracts give an oil (10.3 g) which was purified on a silica column by elution with a mixture of chloroform and methanol to give 6-[2-(2-hydroxy-3-isopropylaminopropoxy)phenyl]-4,5-dihydro-3(2H)-pyridazinone (6.25 g, 66%), m.p. 124°-126°. The hydrochloride, crystallised from 2-propanol, had m.p., 162-5° – 164.5°. Found: C, 55.95; H, 7.19; Cl, 10.28; N, 12.09; $M^+$, 305. $C_{16}H_{24}ClN_3O_3$ requires: C, 56.22; H, 7.08; Cl, 10.37; N, 12.29%; M(base), 305).

(v) A stirred mixture of 6-[2-(2-hydroxy-3-isopropylaminopropoxy)phenyl]-4,5-dihydro-3(2H)-pyridazinone (10g, 0.03 mole), acetic anhydride (50 ml), acetic acid (50 ml) and pyridine (10 drops) was heated in a water bath held at 65°–75°. After 45 minutes, bromine (5.25 g, 0.03 mole) in acetic acid (40 ml) was added dropwise during 45 minutes. Evaporation under reduced pressure gave an oil which was dissolved in dichloromethane and washed with dilute hydrochloric acid and water. The dried organic solution was evaporated to an oil (15 g) which was purified on a silica column by elution with mixtures of chloroform and methanol. 6-[2-(2-Acetoxy-3-N-acetylisopropylaminopropoxy)phenyl]-3-(2H)-pyridazinone was obtained as a glass (8.9 g, 70%) by evaporation under reduced pressure. ($M^+$, 387; M,387)

(vi) Phosphorus pentasulphide (8.5 g, 0.04 mole) was added to a stirred solution of 6-[2-(2-acetoxy-3-N-acetylisopropylaminopropoxy)phenyl-3(2H)-pyridazinone (7.4 g, 0.02 mole) in pyridine (160 ml) and the stirred mixture was heated under reflux for 1 hour. Additional phosphorus pentasulphide (4.25 g, 0.02 mole) was added and the stirred mixture was refluxed for a further hour. The cold supernatant pyridine solution was decanted (from a viscous oil), diluted with water and evaporated. The residue was dissolved in dichloromethane and washed with dilute hydrochloric acid and water. Evaporation of the dried organic solution gave an orange gum (7g) which was separated on a silica column by elution with mixtures of chloroform and methanol into 6-[2-(2-acetoxy-3-N-thioacetylisopropylaminopropoxy)phenyl]-3(2H)-pyridazinethione (yellow glass, 4.2 g, 52%) and 6-[2-(2-acetoxy-3-N-acetylisopropylaminopropoxy)phenyl]-3(2H)-pyridazinethione (yellow glass, 2.0 g, 26%). ($M^+$ (acetyl, 403; M 403. $M^{+\ (thioacetyl)}$, 419; M 419)

(vii) Aqueous sodium hydroxide solution (N/1, 57.2 ml) was added to a stirred solution of 6-[2-(2-acetoxy-3-N-thioacetylisopropylaminopropoxy)phenyl]-3(2H)-pyridazinethione (6 g, 0.014 mole) in methanol and the mixture was heated under reflux for 90 minutes. Sodium hydroxide (0.56 g, 0.014 mole) was added and the stirred mixture was refluxed for a further 2.5 hours. The residue after evaporation was dissolved in a small volume of water and the stirred solution was neutralised with 25% aqueous acetic acid to give a pale yellow precipitate, which was collected and washed with water (4.23 g, 92%, m.p. 162°–164° C).

Recrystallisation from water gave 6-[2-(2-hydroxy-3-isopropylaminopropoxy)phenyl]-3(2H)-pyridazinethione (m.p. 165.5°–167.5°). This product was also similarly prepared from 6-[2-(2-acetoxy-3-N-acetylisopropylamino-propoxy)phenyl]-3(2H)-pyridazinethione. (Found: C, 60.15; H, 6.83; N, 13.2; $M^+$, 319. $C_{16}H_{21}N_3O_2$ requires: C, 60.20; H, 6.63; N, 13.15%; M, 319).

(viii) A stirred mixture of 6-[2-(2-hydroxy-3-isopropylaminopropoxy)phenyl]-3(2H)-pyridazinethione (1.5 g, 0.005 mole) and hydrazine hydrate (30 ml) was heated under reflux in an atmosphere of nitrogen for 90 minutes. Excess of hydrazine hydrate was removed under reduced pressure and 3-hydrazino-6-[2-(2-hydroxy-3-isopropylaminopropoxy)phenyl]-pyridazine was isolated as the amorphous citrate (2 g, 83%). (Found: C, 51.34; H, 5.93; N, 13.00; $C_{16}H_{23}N_5O_2.C_6H_8O_7.\frac{1}{2}CH_3OH$ requires: C, 51.40; H, 6.33; N, 13.32%).

EXAMPLE 2

Preparation of 6-[2-(3-t-Butylamino-2-hydroxypropoxy)phenyl]-3(2H)-pyridazinethione (i) A stirred mixture of methyl 3-[2-(2,3-epoxypropoxy)benzoyl]propionate (54.75 g, 0.21 mole), methanol (580 ml) and t-butylamine (140 ml, 1.31 mole) was heated under reflux for 70 minutes. Evaporation of the solution under reduced pressure gave an oil (73 g) which crystallised when allowed to stand. Purification on a silica column by elution with mixtures of chloroform and methanol gave methyl 3-[2-(3-t-butylamino-2-hydroxypropoxy)benzoyl]propionate (55.4 g, 80%) which after recrystallisation from benzene - petroleum ether (b.p. 60°–80°) had m.p. 80°–81.5°. (Found: C, 63.63; H, 7.99; N, 3.90: $M^+$, 337. $C_{18}H_{27}NO_5$ requires: C, 64.09; H, 8.07; N, 4.15%, M, 337)

(ii) Hydrazine hydrate (22 ml, 0.44 mole) was added to a stirred solution of methyl 3-[2-(3-t-butylamino-2-hydroxypropoxy)benzoyl]propionate (48.8 g; 0.14 mole) in glacial acetic acid (500 ml) and the solution was heated under reflux for 90 minutes. Evaporation under reduced pressure gave an oil (127 g) which was dissolved in water, treated with an excess of sodium carbonate solution and extracted with dichloromethane. Evaporation of the dried extracts gave an oil (49 g) which was purified on a silica column by elution with mixtures of chloroform and methanol to give 6-[2-(3-t-butylamino-2-hydroxypropoxy)phenyl]-4,5-dihydro-3(2H)-pyridazinone (33.44 g, 72%, m.p. 138°–141°). The hydrochloride, crystallised from ethanol-ether, had m.p. 201°–203°. (Found: C, 57.18; H, 7.41; Cl, 9.67; N, 11.39; $M^+$, 319. $C_{17}H_{25}N_3O_3$. HCl requires: C, 57.36; H, 7.36; Cl, 9.96; N, 11.81; M(base), 319).

(iii(a)) A stirred mixture of 6-[2-(3-t-butylamino-2-hydroxypropoxy)phenyl]-4,5-dihydro-3(2H)-pyridazinone (15 g, 0.047 mole), acetic anhydride (100 ml) potassium carbonate (6.5 g, 0.047 mole) and pyridine (15 drops) was heated in a water bath whose temperature was raised from 50° to 100° during 60 minutes. Acetic acid (100 ml) was added and the stirred mixture was heated in a water bath held at 75°. Bromine (7.52 g, 0.047 mole) in acetic acid (30 ml) was added dropwise during 60 minutes, and the mixture was heated for an additional 20 minutes. The residue after evaporation ws dissolved in dichloromethane and washed with water. Evaporation of the dried organic solution gave a glass (17.4 g, 92%) which was purified on a silica column by elution was mixtures of chloroform and methanol to give 6-[2-(2-acetoxy-3-N-acetyl-t-butylaminopropoxy)-phenyl]-3(2H)pyridazinone (13.3 g, 70%) obtained as a glassy foam by evaporation under reduced pressure. (Found: $M^+$, 401; $C_{21}H_{27}N_3O_5$. requires: M, 401).

(iii(b)) A stirred mixture of 6-[2-(3-t-butylamino-2-hydroxypropoxy)phenyl]-4,5-dihydro-3(2H)-pyridazinone (7.0 g, 0.022 mole) and sodium 3-nitrobenzenesulphonate (4.93 g, 0.022 mole) in sodium hydroxide solution (2.2 g, 0.055 mole, in 70 ml of water) was heated under reflux for 100 minutes. Hydrochloric acid was added to the cold stirred solution to pH 8, then an excess of potassium carbonate was added. 6-[2-(3-t-Butylamino-2-hydroxypropoxy)phenyl]-3(2H)-pyridazinone (5.2 g, 75%, m.p. 104°–114° C) was collected, washed with water and recrystallised from 50% aqueous ethanol. The hydrochloride, crystallised from methanol-ether, had m.p. 257°–260° C. (Found: C, 57.52; H, 6.82; Cl, 9.98; N, 11.79 $C_{17}H_{23}N_3O_3 \cdot HCl$ requires: C, 57.70; H, 6.84; Cl, 10.02; N, 11.33%).

A stirred mixture of 6-[2-(3-t-butylamino-2-hydroxypropoxy)-phenyl]-3(2H)-pyridazinone (5.2 g, 0.016 mole), potassium carbonate (6.8 g, 0.049 mole), and acetic anhydride (27 ml), was heated for 1 hour in a water bath at 70° C. After evaporation under reduced pressure the residue was distributed between water and dichloromethane. The aqueous phase was washed with dichloromethane and the combined organic solution was washed with water, dilute hydrochloric acid, and again with water. Evaporation of the dried organic solution gave 6-[2-(2-acetoxy-3-N-acetyl-t-butylaminopropoxy)phenyl]-3(2H)-pyridazinone (6.0 g, 91%).

(iv) Phosphorus pentasulphide (9g, 0.04 mole) was added to a stirred solution of 6-[2-(2-acetoxy-3-N-acetyl-t-butylaminopropoxy)phenyl]-3(2H)-pyridazinone (8.14 g, 0.02 mole) in dry pyridine (160 ml) and the stirred mixture was heated under reflux for 1.75 hours. Additional phosphorus pentasulphide (3 g, 0.013 mole) was added to the partly cooled mixture which was then refluxed for a further 1.75 hours. When cool the supernatant pyridine solution was decanted (from a viscous oil) and diluted with an equal volume of water. After evaporation, the residue was dissolved in dichloromethane and washed with dilute hydrochloric acid and with water. Evaporation of the dried organic solution gave a yellow foam (8.16 g, 96%). Purification on a silica column by elution with mixtures of chloroform and methanol gave 6-[2-(2-acetoxy-3-N-acetyl-t-butylaminopropoxy)phenyl]-3(2H)-pyridazinethione (7.44 g, 88%) as a yellow foam after evaporation under reduced pressure. (Found: $M^+$, 417. $C_{21}H_{27}N_3O_4S$ requires M, 417).

(v) Aqueous sodium hydroxide solution (N/1, 71.4 ml) was added to a stirred solution of 6-[2-(2-acetoxy-3-N-acetyl-t-butylaminopropoxy)phenyl]-3(2H)-pyridazinethione (7.44 g, 0.018 mole) in methanol (110 ml) and the mixture was heated under reflux for 30 minutes. The residue after evaporation was dissolved in water and the solution treated with 25% aqueous acetic acid to give pale yellow precipitate, which ws collected and washed with water (5.64 g, 95% m.p. 184°-186.5°). Recrystallisation from aqueous ethanol gave 6-[2-(3-t-butylamino-2-hydroxypropoxy)phenyl]-3(2H)-pyridazinethione, m.p. 186.5°-189°. (Found: C, 61.50; H, 6.78; N, 12.44; $M^+$, 333. $C_{17}H_{23}N_3O_2S$ requires: C, 61.23; H, 6.95; N, 12.60% M, 333).

(vi) A stirred mixture of 6-[2-(3-t-butylamino-2-hydroxypropoxy)phenyl]-3(2H)-pyridazinethione (2 g, 0.006 mole) and hydrazine hydrate (50 ml) was heated under reflux in an atmosphere of nitrogen for 90 minutes. Excess of hydrazine hydrate was removed under reduced pressure and 3-[2-(3-t-butylamino-2-hydroxypropoxy)phenyl]-6-hydrazinopyridazine was isolated as the hemisulphate hemihydrate (2.34 g, 98%, m.p. 180°-185°). Recrystallisation from aqueous ethanol gave a crystalline material of m.p. 200°-203° (decomposition). (Found: C, 52.41; H, 6.76; N, 17.78; $M^+$, 331. $C_{17}H_{25}N_5O_2 \cdot \frac{1}{2}H_2SO_4 \cdot \frac{1}{2}H_2O$ requires: C, 52.43; H, 6.99; N, 17.98%; M(base), 331).

EXAMPLE 3

Preparation of
6-[2-(3-t-Butylamino-2-hydroxypropoxy)-4-methylphenyl]-3-(2H)-pyridazinethione.

(i) 3-(2-Hydroxy-4-methylbenzoyl)propionic acid was esterified with methanol-hydrogen chloride, in a similar manner to the procedure described in Example 1(i), to give methyl 3-(2-hydroxy-4-methylbenzoyl)propionate, m.p. 61°-63°.

(ii) Methyl 3-(2-hydroxy-4-methylbenzoyl)propionate was reacted with epibromohydrin in a similar manner to the procedure described in Example 1(ii) to give methyl 3-[2-(2,3-epoxypropoxy)-4-methylbenzoyl]propionate, m.p. 61.5°-63°.

(iii) Methyl 3-[2-(2,3-epoxypropoxy)-4-methylbenzoyl]-propionate was treated with t-butylamine in a similar manner to the procedure described in Example 2(i) to give methyl 3-[2-(3-t-butylamino-2-hydroxypropoxy)-4-methylbenzoyl]-propionate, m.p. 82°-84.5°.

(iv) Methyl 3-[2-(3-t-butylamino-2-hydroxypropoxy)-4-methylbenzoyl]propionate was cyclised with hydrazine hydrate in a manner similar to that described in Example 2(ii) to give 6-[2-(3-t-butylamino-2-hydroxypropoxy)-4-methylphenyl]-4,5-dihydro-3(2H)-pyridazinone (m.p. 129.5°-130.5° C). The hydrochloride, crystallised from ethanol-ether, had m.p. 206.5°-209.5° C.

(v) By subjecting 6-[2-(3-t-butylamino-2-hydroxypropoxy)-4-methylphenyl]-4,5-dihydro-3(2H)-pyridazinone to a process similar to that described in Example 2(iii)a, 6-[2-(2-acetoxy-3-N-acetyl-t-butylaminopropoxy)-4-methylphenyl]-3(2H)-pyridazinone may be prepared; it may also be obtained by a process similar to that described in Example 2(iii)b, i.e., by acetylation of the intermediate 6-[2-(3-t-butylamino-2-hydroxypropoxy)-4-methylphenyl]-3(2H)-pyridazinone (m.p. 180°-181° C).

(vi) 6-[2-(2-Acetoxy-3-N-acetyl-t-butylaminopropoxy)-4-methylphenyl]-3(2H)-pyridazinone was treated with phosphorus pentasulphide in a similar manner to that described in Example 2(iv) to give 6-[2-(2-acetoxy-3-N-acetyl-t-butylaminopropoxy)-4-methylphenyl]-3(2H)-pyridazinethione which, recrystallised from methanol, had m.p. 162.5°-164° C. (Found: C, 61.36; H, 6.63; N, 9.64; S, 7.57; $C_{22}H_{29}N_3O_4S$ requires: C, 61.20; H, 6.77; N, 9.73; S, 7.43%)

(vii) 6-[2-(2-Acetoxy-3-N-acetyl-t-butylaminopropoxy)-4-methylphenyl]-3(2H)pyridazinethione was hydrolysed in a manner similar to that described in Example 2(v) to give 6-[2-(3-t-butylamino-2-hydroxypropoxy)-4-methylphenyl]-3(2H)-pyridazinethione which, recrystallised frm 2-methoxyethanol, had m.p. 135°-140° C.

In a similar manner 6-[2-(3-t-butylamino-2-hydroxypropoxy)-4-ethylphenyl]-3(2H)-pyridazinethione, m.p. 96°-99° C was prepared from 3-(4-ethyl-2-hydroxybenzoyl)propionic acid, m.p. 152°-153.5° C, via 6-[2-(3-t-butylamino-2-hydroxypropoxy)-4-ethylphenyl]-4,5-dihydro-3(2H)-pyridazinone, m.p. 138°-139°.

EXAMPLE 4

6-[2-(3-t-Butylamino-2-hydroxypropoxy)-4-chlorophenyl]-3(2H)-pyridazinethione (i) Hydrogen chloride was bubbled into a gently boiling solution of 3-(4-chloro-2-hydroxybenzoyl)propionic acid (12.0 g, 0.053 mole) in dry ethanol (21.2 cc) until esterification was complete. The product crystallised from ether to give ethyl 3-(4-chloro-2-hydroxybenzoyl)-propionate (13.29 g, 98% m.p. 68°-69°) (Found: C, 56.07; H, 5.06; Cl, 13.69; $M^+$, 256/258. $C_{12}H_{13}ClO_4$ requires: C, 56.15; H, 5.10; Cl, 13.81%; M, 256/258).

(ii) A well stirred mixture of ethyl 3-(4-chloro-2-hydroxybenzoyl)propionate (9.6 g, 0.037 mole), potassium carbonate (5.96 g, 0.043 mole) epibromhydrin (14.4 ml, 0.173 mole) and dry butan-2-one (250 ml) was heated under reflux for 28 hours. Evaporation of the filtered solution under reduced pressure and purification of the residue by column chromatography gave ethyl 3-[4-chloro-2-(2,3-epoxypropoxy)benzoyl]-propionate as an oil (10.0 g, 86%). (Found: M+, 312/314. $C_{15}H_{17}ClO_5$. requires M, 312/314).

(iii) A sitrred mixture of ethyl 3-[4-chloro-2-(2,3-epoxypropoxy)benzoyl]propionate (3.0 g, 0.01 mole) methanol (28 ml) and t-butylamine (6.7 ml, 0.0625 mole) was heated under reflux for 70 minutes. The mixture was evaporated to an oily residue which was purified on a silica column by elution with mixtures of chloroform and methanol and recrystallisation from etherpetroleum ether (b.p. 40°-60°) to give ethyl 3-[2-(3-t-butylamino-2-hydroxypropoxy)-4-chlorobenzoyl]propionate (3.18 g, 88%, m.p. 70°). (Found: C, 58.93; H, 7.16; Cl, 9.64; N, 3.63; M+, 385/387. $C_{19}H_{28}ClNO_5$ requires; C, 59.14; H 7.13; Cl, 9.19; N, 3.63%; M, 385/387).

(iv) Hydrazine hydrate (1.57 ml, 0.0314 mole) was added to a stirred solution of ethyl 3-[2-(3-t-butylamino-2-hydroxypropoxy)-4-chlorobenzoyl]propionate (2.4 g, 0.0065 mole) in glacial acetic acid (36 ml) and the solution was heated under reflux for 90 minutes. Evaporation under reduced pressure gave an oil which was dissolved in water, treated with an excess of aqueous sodium carbonate solution and the mixture was extracted with dichloromethane. Evaporation of the dried or ganic extracts gave an oil which was purified on a silica column by elution with mixtures of chloroform and methanol to give 6-[2-(3-t-butylamino-2-hydroxypropoxy)-4-chlorophenyl]-4,5-dihydro-3(2H)-pyridazinone (1.1 g, 50%, m.p. (195°). The hemisulphate, crystallised from ethanol, had m.p. 250° (decomposition). (Found: C, 50.19; H, 6.21; Cl, 8.75; N, 10.11; S, 3.89; M+, 353/355. $C_{17}H_{24}ClN_3O_3.0.53\ H_2SO_4$ requires; C, 50.31; H. 5.96; Cl, 8.74; N, 10.35; S, 4.17%; M(base), 353/355).

(v) By subjecting 6-[2-(3-t-butylamino-2-hydroxypropoxy)-4-chlorophenyl]-4,5-dihydro-3(2H)-pyridazionone to a similar series of reactions to that described in Example 2(iii-v) the title compound m.p. 195°–198° was prepared.

In a similar manner 6-[2-(3-t-Butylamino-2-hydroxypropoxy-4-bromophenyl]-3(2H)-pyridazinethione may be prepared from 3-(4-bromo-2-hydroxybenzoyl)propionic acid.

In a similar manner 6-[2-(3-t-butylamino-2-hydroxypropoxy)-4-fluorophenyl]-3(2H)-pyridazinethione m.p. 187°–190° was prepared from 3-(4-fluoro-2-hydroxybenzoyl)propionic acid.

EXAMPLE 5

Preparation of 6-[2-(3-t-Butylamino-2-hydroxypropoxy)-6-fluorophenyl]-3(2H)-pyridazinethione (i) A cold solution of 2-fluoro-6-methoxylithiobenzene in ether was added to a cold dilute benzene solution of β-carbomethoxypropionyl chloride and the resulting complex was decomposed with ammonium chloride solution to give methyl 3-(2-fluoro-6-methoxybenzoyl)propionate.

(ii) Methyl 3-(2-fluoro-6-methoxybenzoyl)propionate was demethylated with aluminium chloride in chlorobenzene and 3-(2-fluoro-6-hydroxybenzoyl)propionic acid was isolated.

(iii) By subjecting 3-(2-fluoro-6-hydroxybenzoyl)propionic acid to a series of reactions similar to those described in Example 1(i-ii) and 2(i-v), the title compound may be prepared.

EXAMPLE 6

Preparation of 6-[2-(3-t-Butylamino-2-hydroxypropoxy)-5-trifluoromethylphenyl]-3(2H)-pyridazinethione (i) A solution of 2-methoxy-5-trifluoromethylphenyllithium in ether was added to a cold stirred solution of N-methylsuccinimide in benzene. The resultant mixture was allowed to stand overnight and was then decomposed with ammonium chloride solution to give N-methyl 3-(2-methoxy-5-trifluoromethylbenzoyl)propionamide.

(ii) N-Methyl 3-(2-methoxy-5-trifluoromethylbenzoyl)-propionamide was demethylated with hydrogen bromide in acetic acid and 3-(2-hydroxy-5-trifluoromethylbenzoyl)-propionic acid was isolated.

(iii) By subjecting 3-(2-hydroxy-5-trifluoromethylbenzoyl)-propionic acid to a series of reactions similar to those described in Examples 1(i-ii) and 2(i-v), the title compound may be prepared.

EXAMPLE 7

Preparation of 6-[2-(3-t-Butylamino-2-hydroxypropoxy)-6-methoxyphenyl]-3(2H)-pyridazinethione (i) A solution of 1,3-dimethoxybenzene (89 ml, 0.064 mole) in dry tetrahydrofuran (480 ml) was added during 10 minutes to a stirred solution of n-butyl lithium in hexane (350 ml, 0.6 mole) under an atmosphere of nitrogen. The stirred mixture was heated under reflux for 90 minutes, then a solution of N-methyl succinimide (77 g, 0.68 mole) in dry tetrahydrofuran was added dropwise. The mixture was heated under reflux for an additional hour and then allowed to stand overnight. The supernatant was decanted and the residue was hydrolysed with 20% aqueous ammonium chloride solution (280 ml) and extracted with chloroform. The washed and dried extract was evaporated and the residue recrystallised from ethyl acetate to give N-methyl 3-(2,6-dimethoxybenzoyl)-propionamide (15 g, 10%, m.p. 134°). (Found: C, 62.18; H, 6.73; N, 5.54; $C_{13}H_{17}NO_4$ requires C, 62.14; H, 6.82; N, 5.57%).

(ii) N-Methyl 3-(2,6-dimethoxybenzoyl)propionamide was demethylated with aluminium chloride in chlorobenzene to give N-methyl 3-(2-hydroxy-6-methoxybenzoyl)propionamide, m.p. 125° which may also be prepared from a by-product, N-methyl 3-(2,6-dihydroxybenzoyl)propionamide, by selective methylation with methyl iodide and potassium carbonate in acetone. (iii) By subjecting N-methyl 3-(2-hydroxy-6-methoxybenzoyl)-propionamide to a series of reactions similar to those described in Examples 1(i-ii) and 2(i-v), the title compound may be prepared.

EXAMPLE 8

Preparation of 6-[2-(3-t-Butylamino-2-hydroxypropoxy)-5-cyanophenyl]-3(2H)-pyridazinethione (i) Aluminium chloride (148 g, 1.11 mole) was added to a stirred mixture of 4-cyanophenol (44 g, 0.37 mole), succinic anhydride (33.3 g, 0.33 mole), and sym-tetrachloroethane (260 ml), and the mixture was then heated at 135° for 2 hours. The resultant complex was decomposed with ice and hydrochloric acid, and 3-(5-cyano-2- hydroxybenzoyl)propionic acid was isolated by standard procedures.

(ii) 3-(5-Cyano-2-hydroxybenzoyl)propionic acid was subjected to a series of reactions similar to those described in Example 1(i-ii) and 2(i-ii), to give 6-[2-(3-t-butylamino-2-hydroxypropoxy)-5-cyanophenyl]-4,5-dihydro-3(2H)-pyridazinone.

(iii) A mixture of 6-[2-(3-t-butylamino-2-hydroxypropoxy)-5-cyanophenyl]-4,5-dihydro-3(2H)-pyridazinone and chloramil was heated under reflux in n-butanol to give 6-[2-(3-t-butylamino-2-hydroxypropoxy)-5-cyanophenyl]-3(2H)-pyridazinone.

(iv) 6-[2-(3-t-Butylamino-2-hydroxypropoxy)-5-cyanophenyl]-3(2H)-pyridazinone was acetylated with a mixture of acetic anhydride and potassium carbonate to give 6-[2-(2-acetoxy-3-N-acetyl-t-butylaminopropexy)-5-cyanophenyl]-3(2H)-pyridazinone.

(v) By subjecting 6-[2-(2-acetoxy-3-N-acetyl-t-butylaminopropoxy)-5-cyanophenyl]-3(2H)-pyridazinone to a series of reactions similar to those described in Example 2 (iv-v), the title compound may be prepared.

EXAMPLE 9

Preparation of 6-[5-Carboxamidomethyl-2-(2-hydroxy-3-isopropylaminopropoxy)phenyl]-3(2H)-pyridazinethione (i) 4-Hydroxybenzyl cyanide was reacted with succinic anhydride and aluminium chloride in a similar manner to that described in Example 11(i) to give 3-(5-cyanomethyl-2-hydroxybenzoyl)-propionic acid.

(ii) 3-(5-Cyanomethyl-2-hydroxybenzoyl)propionic acid was subjected to a series of reactions similar to those described in Example 1(i-vi) to give 6-[5-cyanomethyl-2-(2-hydroxy-3-isopropylaminopropoxy)-phenyl]-3-(2H)-pyridazinethione.

(iii) 6-[5-Cyanomethyl-2(2-hydroxy-3-isopropylaminopropoxy)-phenyl]-3(2H)-pyridazinethione was dissolved in cold concentrated sulphuric acid and the solution poured into ice-water and neutralised to give 6-[5-carboxamidomethyl-2-(2-hydroxy-3-isopropylaminopropoxy)phenyl]-3(2H)-pyridazinethione.

EXAMPLE 10

6-[5-Amino-2-(3-t-butylamino-2-hydroxypropoxy)-phenyl]-3(2H)-pyridazinethione (i) Nitric acid (d. 1.52; 50 ml) was added dropwise to a stirred suspension of 3-(2-hydroxybenzoyl)propionic acid (30 g, 0.155 mole) in glacial acetic acid (250 ml) at 5°–10°. The temperature was allowed to rise slowly, at 30°–35° an exothermic reaction took place and cooling was necessary to keep the temperature of the reaction mixture below 45°, the resulting solution was stirred for a further 60 minutes and then poured into ice-water (750 ml). The yellow precipitate, a crude mixture of 3-(2-hydroxy-5-nitrobenzoyl)propionic acid and 3-(2-hydroxy-3-nitrobenzoyl)propionic acid, was washed with water and dried (36.0 g, 97% m.p. 152°–156°). (Found: M+, 239. $C_{10}H_9NO_6$ requires: M, 239).

(ii) The above mixture of acids (60 g, 0.25 mole) was dissolved in dry methanol (800 ml) and hydrogen chloride gas was passed through the gently boiling solution for 2 hours. The solvent was evaporated under reduced pressure, the residue in chloroform (200 ml) was washed with aqueous sodium bicarbonate (200 ml) and with water. The dried solution was evaporated under reduced pressure to give a solid (55 g) which was separated into the isomeric esters on a silica column by elution with chloroform-methanol mixtures. The methyl 3-(2-hydroxy-5-nitrobenzoyl)-propionate (25.3 g, 40%) was crystallised from carbon tetrachloride as needles (m.p. 90°–93°). (Found: C, 52.16; H, 4.36; N, 5.38; M+, 253. $C_{11}H_{11}NO_6$ requires: C, 52.17; H, 4.38; N, 5.53%; M, 253).

(iii) Methyl 3-(2-hydroxy-5-nitrobenzoyl)propionate (19.0 g, 0.075 mole) was dissolved in sodium hydroxide solution (2N; 600 ml) and heated on a steam bath for 1 hour. Acidification of the cooled solution with dilute hydrochloric acid gave 3-(2-hydroxy-5-nitrobenzoyl)-propionic acid which was washed with water and dried (17.4 g, 97%, m.p. 175°–178°).

(iv) A solution of 3-(2-hydroxy-5-nitrobenzoyl)propionic acid (5.5 g, 0.023 mole) in ammonium hydroxide solution (5N; 100 ml) was added to a stirred, boiling solution of ferrous sulphate heptahydrate (45 g, 0.161 mole) in water (200 ml). Stirring under reflux was continued for a further 1 hour, ammonium hydroxide solution was added to pH 9, the mixture was filtered through Kieselguhr and evaporated to dryness. The solid residue was crystallised from ethanol to give pale yellow needles of 3-(5-amino-2-hydroxybenzoyl)propionic acid (2.2 g, 46% m.p. 158°–160°). (Found: M+, 209. $C_{10}H_{11}NO_4$ requires: M, 209).

(v) Sodium hydroxide solution (0.2 N) was added to 3-(5-amino-2-hydroxybenzoyl)propionic acid (2.4 g, 0.0115 mole) until the solid dissolved. Acetic anhydride (3.0 ml) was quickly added to the solution (pH 10) with vigorous stirring at 10°–15°, after which the pH was in the range 4–5, and stirring was continued for a further hour. The precipitated solid ws collected and washed with water, and a second crop was obtained by evaporation of the filtrate and addition of water to the residue. The combined solids were recrystallised from ethanol to give 3-(5-acetamido-2-hydroxybenzoyl)propionic acid (2.2 g, 76%, m.p. 205°–206°). (Found: C, 57.13; H, 5.25; N, 5.57; M+, 251. $C_{12}H_{13}NO_5$ requires C, 57.37; H, 5.22; N, 5.58%; M, 251).

(vi) Hydrogen chloride gas was passed through a gently boiling solution of 3-(5-acetamido-2-hydroxybenzoyl)propionic acid (1.2 g, 0.0048 mole) in dry methanol (20 ml) until esterification was complete. The reaction mixture was poured into ice-water and extracted with chloroform. The extract was washed with sodium bicarbonate solution and water, dried and evaporated to give methyl 3-(5-acetamido-2-hydroxybenzoyl)propionate (0.75 g, 59%, m.p. 145°–147°). (Found: M+, 265. $C_{13}H_{15}NO_5$ requires: M, 265).

(vii) Methyl 3-(5-acetamido-2-hydroxybenzoyl)propionate (0.75 g, 0.0028 mole) anhydrous potassium carbonate (0.39 g, 0.0028 mole), epibromohydrin (0.78 g, 0.00565 mole) and dry ethyl methyl ketone (20 ml) were stirred and heated under reflux for 16 hours. The cooled mixture was filtered and evaporated under reduced pressure to an oil which was purified by elution from a silica column with chloroform-methanol to give methyl 3-[5-acetamido-2-(2,3-epoxypropoxy)-benzoyl]propionate (0.52 g, 57%, m.p. 84°–87°). (Found: M+, 321, $C_{16}H_{19}NO_6$ requires M, 321).

(viii) A solution of methyl 3-[5-acetamido-2-(2,3-epoxypropoxy)benzoyl]propionate (0.52 g, 0.0016 mole), t-butylamine (20 ml) and methanol (10 ml) was heated under reflux for 16 hours. Evaporation of the reaction mixture left an oil which was dissolved in ethanol and treated with ether to give crystalline methyl 3-[5-acetamido-2-(3-t-butylamino-2-hydroxypropoxy)- benzoyl]propionate (0.21 g, 33%; m.p. 127°–128°). (Found; M+, 394. $C_{20}H_{30}N_2O_6$ requires: M, 394).

(ix) Hydrazine hydrate (0.0785 ml, 0.00157 mole) was added to a stirred solution of methyl 3-[5-acetamido-2-(3-t-butylamino-2-hydroxypropoxy)benzoyl]propionate (0.21 g, 0.0005 mole) in glacial acetic acid (2 ml) and the solution was heated under reflux for 90 minutes. The residue after evaporation was treated with an excess of sodium bicarbonate solution and the solution evaporated to dryness under reduced pressure. The residue was extracted with dichloromethane and the dried extract evaporated to dryness. An aqueous solution of the residue was washed with two small portions of dichloromethane and then evaporated to an oily residue, which with ethyl acetate gave 6-[5-acetamido-2-(3-t-butylamino-2-hydroxypropoxy)phenyl]-4,5-dihydro-3(2H)-pyridazinone (0.16 g, 80%, m.p. 165°–168°).

(x) 6-[5-Acetamido-2-(3-t-butylamino-2-hydroxypropoxy)phenyl]-4,5-dihydro-3(2H)-pyridazinone was reacted with chloranil in boiling butanol to give 6-[5-acetamido-2-(3-t-butylamino-2-hydroxypropoxy)-phenyl]-3(2H)-pyridazinone.

(xi) A solution of 6-[5-acetamido-2-(3-t-butylamino-2-hydroxypropoxy)phenyl]-3(2H)-pyridazinone in acetic anhydride containing potassium carbonate was heated on a steam bath for 1 hour to give 6-[5-acetamido-2-(2-acetoxy-3-N-acetyl-t-butylamino)phenyl]-3(2H)-pyridazinone.

(xii) A stirred mixture of 6-[5-acetamido-2-acetoxy-3-N-acetyl-t-butylamino)phenyl]-3(2H)-pyridazinone, phosphorus pentasulphide and pyridine was heated under reflux for 3 hours and the reaction mixture evaporated under reduced pressure. Purification of the product by elution with dichloromethane-methanol mixtures from a silica column gave fractions which contained 6-[5-acetamido-2-(2-acetoxy-3-N-acetyl-t-butylamino)-phenyl]-3(2H)-pyridazinethione and 6-[2-(2-acetoxy-3-N-acethyl-t-butylamino)-5-thioacetamidophenyl]-3(2H)-pyridazinethione.

(xiii) Hydrolysis of the two column fractions from (xii) with sodium hydroxide in boiling methanol followed by neutralisation and evaporation of the reaction mixture gave 6-[5-amino-2-(3-t-butylamino-2-hydroxypropoxy)phenyl]-3(2H)-pyridazinethione.

EXAMPLE 11

6-[5-Acetamido-2-(3-t-butylamino-2-hydroxypropoxy)phenyl]-3(2H)-pyridazinethione.

Addition of acetic anhydride to a stirred suspension of 6-[5-amino-2-(3-t-butylamino-2-hydroxypropoxy)-phenyl]-3(2H)-pyridazinethione in an aqueous buffer solution at pH 5.5 gave 6-[5-acetamido-2-(3-t-butylamino-2-hydroxypropoxy)phenyl]-3-(2H)-pyridazinethione.

EXAMPLE 12

6-[2-(2-hydroxy-3-t-butylaminopropoxy)-5-(methylamino)phenyl]-3(2H)-pyridazinethione (i) 3-[5-Amino-2-(3-t-butylamino-2-hydroxypropoxy)benzoyl]-propionic acid, prepared by hydrolysis of the product of Example 10 (viii), was esterified with hydrogen chloride in methanol. Evaporation of the solution under reduced pressure gave a residue which was dissolved in the minimum quantity of water, the solution was neutralised with sodium carbonate and extracted with dichloromethane. The extrace was washed with saturated brine, dried and evaporated to give methyl 3-[5-amino-2-hydroxy-3-t-butylaminopropoxy)benzoyl]-propionate.

(ii) A solution of methyl 3-[5-amino-2-(2-hydroxy-3-t-butylaminopropoxy)benzoyl]propionate in dichloromethane was treated with excess of trifluoroacetic anhydride and potassium carbonate and the mixture was stirred until the reaction was complete. Water was added and the aqueous phase was extracted with dichloromethane. The extract was washed with water, dried and evaporated to give methyl 3-[5-trifluoroacetylamino-2-(2-trifluoroacetoxy-3-N-trifluoroacetyl-t-butylaminopropoxy)benzoyl]propionate.

(iii) Methyl 3-[5-trifluoroacetylamino-2-(2-trifluoroacetoxy-3-N-trifluoroacetyl-t-butylaminopropoxy)benzoyl]-propionate was heated under reflux for 10 minutes with an excess of methyl iodide and powdered potassium hydroxide in dry acetone. Methyl iodide and the solvent were removed under reduced pressure and the residue, in water, was heated under reflux for 10 minutes. The solution was neutralised and evaporated with hot ethanol, and the extracts were evaporated under reduced pressure to give 3-[2-(2-hydroxy-3-t-butylaminopropoxy)-5-(methylamino)benzoyl]propionic acid.

(iv) 3-[2-(2-Hydroxy-3-t-butylaminopropoxy)-5-(methylamino)benzoyl]propionic acid was cyclised by a method similar to that described in Example 10 (ix), to give 6-[2-(2-hydroxy-3-t-butylaminopropoxy)-5-(methylamino)phenyl]-4,5-dihydro-3(2H)-pyridazinone.

(v) 6-[2-(2-Hydroxy-3-t-butylaminopropoxy)-5-(methylamino)-phenyl]-4,5-dihydro-3(2H)-pyridazinone was treated with acetic anhydride in a manner similar to that described in Example 11 (i) to give 6-[5-N-acetyl(-methylamino)-2-(2-hydroxy-3-t-butylaminopropoxy)-phenyl]-4,5-dihydro-3-(2H)-pyridazinone.

(vi) 6-[5-N-Acetyl(methylamino)-2-(2-hydroxy-3-t-butylaminopropoxy)phenyl]-4,5-dihydro-3(2H)-pyridazinone was employed in a sequence of reactions similar to those described in Example 10 (x-xiii) to give the title compound.

EXAMPLE 13

Preparation of 6-[2-(3-t-Butylamino-2-hydroxypropoxy)-5-nitrophenyl]-3(2H)-pyridazinethione By subjecting methyl 3-(2-hydroxy-5-nitrobenzoyl)-propionate (prepared as in Example 10 (ii) to a series of reactions similar to those described in Example 1 (ii) and 2 (i-v), the title compound may be prepared.

EXAMPLE 14

Preparation of 6-[2-(3-t-Butylamino-2-hydroxypropoxy)-5-dimethylaminophenyl]-3(2H)-pyridazinethione (i) A stirred mixture of 6-[2-(2-acetoxy-3-N-acetyl-t-butylaminopropoxy)-5-nitrophenyl]-3(2H)-pyridazinone (from Example 13), ethanol, cyclohexene, and 10% palladium o charcoal, was heated under reflux for 16 hours to give 6-[5-amino-2-(2-acetoxy-3-N-acetyl-t-butylaminopropoxy)-phenyl]-3(2H)-pyridazinone.

(ii) 6-[5-Amino-2-(2-acetoxy-3-N-acetyl-t-butylaminopropoxy)-phenyl]-3(2H)-pyridazinone was treated with dimethyl sulphate and sodium acetate in aqueous ethanol to give 6-[2-(2-acetoxy-3-N-acetyl-t-butylaminopropoxy)-5-dimethylaminophenyl]-3(2H)-pyridazinone.

(iii) By subjecting 6-[2-(2-acetoxy-3-N-acetyl-t-butylaminopropoxy)-5-dimethylaminophenyl]-3(2H)-pyridazinone to a series of reactions similar to those described in Example 2(iv-v), the title compound may be prepared.

EXAMPLE 15

Preparation of 6-[2-(3-t-Butylamino-2-hydroxypropoxy)-5-carboxamidophenyl]-3(2H)pyridazinethione (i) Aluminium chloride was added to a stirred mixture of 4-hydroxybenzamide, succinic anhydride, and sym-tetrachloroethane, and the mixture heated at 135° for 2 hours. The complex was decomposed with ice-hydrochloric acid and the solvent steam distilled to give 3-(3-carboxypropionyl)-4-hydroxybenzoic acid.

(ii) 3-(3-Carboxypropionyl)-4-hydroxybenzoic acid was esterified with methanol-hydrogen chloride to give methyl 3-(3-carbomethoxypropionyl)-4-hydroxybenzoate.

(iii) Methyl 3-(3-carbomethoxypropionyl)-4-hydroxybenzoate was subjected to a series of reactions similar to those described in Examples 1(ii) and 2(i) to give methyl 4-(3-t-butylamino-2-hydroxypropoxy)-3-(3-carbomethoxypropionyl) benzoate.

(iv) Methyl 4-(3-t-butylamino-2-hydroxypropoxy)-3-(3-carbomethoxypropionyl)benzoate was heated with dilute sodium hydroxide solution until hydrolysis was complete. The solution was neutralised with acetic acid and then evaporated under reduced pressure. Extraction of the residue with ethanol and evaporation of the extracts gave 4-(3-t-butylamino-2-hydroxypropoxy)-3-(3-carboxypropionyl)benzoic acid.

(v) A solution of equimolar amounts of 4-(3-t-butylamino-2-hydroxypropoxy)-3-(3-carboxypropionyl)benzoic acid and hydrazine hydrate in water was heated under reflux for 16 hours. The volume of the solution was reduced in vacuo to give 4-(3-t-butylamino-2-hydroxypropoxy)-3-(1,4,5,6-tetrahydro-6-oxo-3-pyridazinyl)benzoic acid.

(vi) A mixture of 4-(3-t-butylamino-2-hydroxypropoxy)-3-(1,4,5,6-tetrahydro-6-oxo-3-pyridazinyl)-benzoic acid, chloranil, and n-butanol, was heated under reflux to give 4-(3-t-butylamino-2-hydroxypropoxy)-3-(1,6-dihydro-6-oxo-3-pyridazinyl)benzoic acid.

(vii) 4-(3-t-Butylamino-2-hydroxypropoxy)-3-(1,6-dihydro-6-oxo-3-pyridazinyl)benzoic acid was esterified with ethanol-hyrogen chloride to give ethyl 4-(3-t-butylamino-2-hydroxypropoxy)-3(1,6-dihydro-6-oxo-3-pyridazinyl)benzoate.

(viii) Ethyl 4-(3-t-butylamino-2-hydroxypropoxy)-3-(1,6-dihydro-6-oxo-3-pyridazinyl)benzoate was treated with acetic anhydride in the presence of potassium carbonate to give ethyl 4-(2-acetoxy-3-N-acetyl-t-butylaminopropoxy)-3-(1,6-dihydro-6-oxo-3-pyridazinyl)benzoate.

(ix) Ethyl 4-(2-acetoxy-3-N-acetyl-t-butylaminopropoxy)-3-(1,6-dihydro-6-oxo-3-pyridazinyl)benzoate was subjected to a series of reactions similar to those described in Example 2 (iv-v) to give 4-(3-t-butylamino-2-hydroxypropoxy)-3-(1,6-dihydro-6-thiono-3-pyridazinyl)benzoic acid.

(x) A solution of 4-(3-t-butylamino-2-hydroxypropoxy)-3-[6-thiono-3-pyridazinyl]benzoic acid and ammonia in dioxan was treated with dicyclohexylcarbodiimide to give 6-[2-(3-t-butylamino-2-hydroxypropoxy)-5-carboxamidophenyl]-3(2H)-pyridazinethione.

EXAMPLE 16

Preparation of 6-[2-(3-t-Butylamino-2-hydroxypropoxy)-5-fluorophenyl]-3(2H)-pyridazinethione By subjecting 4-fluorophenol to a series of reactions similar to those described in Examples 8 (i), 1 (i-ii) and 2 (i-v), the title compound may be prepared. 6-[2-(3-t-Butylamino-2-hydroxypropoxy)-5-fluorophenyl]-4,5-dihydro-3(2H)-pyridazinone had m.p. 117°-119° C, 6-[2-(2-acetoxy-3-N-acetyl-t-butylaminopropoxy)-5-fluorophenyl]-3(2H)-pyridazinethione had m.p. 170°-173° C, and 6-[2-(3-t-butylamino-2-hydroxypropoxy)-5-fluorophenyl]-3(2H)-pyridazinethione had m.p. 177°-179°.

EXAMPLE 17

6-[2-(3-t-Butylamino-2-hydroxypropoxy)phenyl]-5-methyl-3(2H)-pyridazinethione (i) A freshly prepared solution of dimethylamine hydrochloride (14.5 g, 0.18 mole) in 37% aqueous formaldehyde solution (10.5 ml, 0.14 mole) was allowed to stand for 30 minutes. Acetic anhydride (80.4 g, 0.77 mole) was then added and the mixture stirred until a clear solution was obtained. To this solution was added 2-benzyloxypropiophenone (28.8 g, 0.12 mole), the stirred mixture was heated under reflux for 2 hours and then evaporated to dryness. Acetone (75 ml) was added to the residue, the mixture was heated under reflux for 5 minutes and the solvent evaporated off. The residue was treated with an excess of dilute sodium hydroxide solution, and the oil which separated was extracted into dichloromethane (3 × 50 ml). The extract was washed with water, dried and evaporated to give a crude mixture (31.4 g) of 1-(2-benzyloxyphenyl)-2-methyl-2-propen-1-one, and N,N-dimethyl 2-(2-benzyloxybenzoyl)-propylamine as an oil.

(ii) The product from (i) above (23.2 g), potassium cyanide (9.13 g, 0.14 mole) and methanol (500 ml) was stirred and heated under reflux for 16 hours. The reaction mixture was then evaporated to dryness, and water and dichloromethane were added to the residue. Evaporation of the washed and dried organic extract gave crude 3-(2-benzyloxybenzoyl)-butyronitrile (20.3 g, 98%) as an oil.

(iii) The crude nitrile from (ii) (20.3 g, 0.073 mole) in 5N hydrochloric acid (600 ml) was stirred and heated under reflux for 2 hours. Evaporation of the mixture gave an oily residue from which 3-(2-hydroxybenzoyl)-butyric acid was isolated by standard procedures as an oil (8.6 g) which was crystallised from cyclohexane (5.2 g, m.p. 95°-97°).

(iv) 3-(2-Hydroxybenzoyl)butyric acid (4.0 g, 0.02 mole) was esterified in methanol in a similar manner to that described in Example 4(i) to give methyl 3-(2-hydroxybenzoyl)butyrate (4.0 g, 94%) as an oil.

(v) Methyl 3-(2-hydroxybenzoyl)butyrate (3.5 g, 0.016 mole) was treated in the manner described in Example 4(ii) to give methyl 3-[2-(2,3-epoxypropoxy)-benzoyl]butyrate as an oil (3.6 g, 86%).

(vi) Methyl 3-[2-(2,3-epoxypropoxy)benzoyl]butyrate (2.4 g, 0.009 mole) was treated in the same manner described in Example 4 (iii) to give methyl 3-[2-(3-t-butylamino-2-hydroxypropoxy)-benzoyl]butyrate as an oil (2.7 g, 88%).

(vii) Methyl 3-[2-(3-t-butylamino-2-hydroxypropoxy)benzoyl]butyrate (2.2 g, 0.0065 mole) was cyclised in the manner described in Example 4(iv) and the product was purified by chromatography to give 6-[2-(3-t-butylamino-2-hydroxypropoxy)-phenyl]-5-methyl-4,5-dihydro-3(2H)-pyridazinone.

(viii) 6-[2-(3-t-Butylamino-2-hydroxypropoxy)-phenyl]-5-methyl-4,5-dihydro-3(2H)-pyridazinone was employed in a sequence of reactions similar to those described in Example 2(ii-vi) to give the title compound.

EXAMPLE 18

6-[2-(3-t-Butylamino-2-hydroxypropoxy)-5-methylphenyl]-3(2H)-pyridazinethione (i) p-Cresol was reacted with succinic anhydride and aluminium chloride in a similar manner to the procedure described in Example 8 (i) to give 3-(5-methyl-2-hydroxybenzoyl)-propionic acid.

(ii) 3-(5-Methyl-2-hydroxybenzoyl)propionic acid was esterified with methanol-hydrogen chloride in a similar manner to the procedure described in Example 1 (i) to give methyl 3-(3-methyl-2-hydroxybenzoyl)-propionate.

(iii) Methyl 3-(5-methyl-2-hydroxybenzoyl)propionate was reacted with epibromohydrin in a similar manner to the procedure described in Example 1(ii) to give methyl 3-[5-methyl-2-(2,3-epoxypropoxy)benzoyl]propionate as an oil.

(iv) Methyl 3-[5-methyl-2-(2,3-epoxypropoxy)benzoyl]propionate was treated with t-butylamine in a similar manner to the procedure described in Example 2(i) to give methyl 3-[2-3(t-butylamino-2-hydroxypropoxy)-5-methylbenzoyl]propionate, which was crystallised from ether-light petroleum, and had m.p. 82.5°-84.5°.

(v) Methyl 3-[2-(3-t-butylamino-2-hydroxypropoxy)-5-methylbenzoyl]propionate was cyclised with hydrazine hydrate in a similar manner to the procedure described in Example 2 (ii) to give 6-[2-(3-t-butylamino-2-hydroxypropoxy)-5-methylphenyl]-4,5-dihydro-3(2H)-pyridazinone, m.p. 126°-127.5°. The hydrochloride had m.p. 206.5°-209.5°.

(vi) 6-[2-(3-t-butylamino-2-hydroxypropoxy)-5-methylphenyl]-4,5-dihydro-3(2H)-pyridazinone was dehydrogenated with sodium nitrobenzenesulphonate to give 6-2-(3-t-butylamino-2-hydroxypropoxy)-5-methylphenyl-3(2H)-pyridazine m.p. 180°-181° which was acetylated to give 6-[2-(2-acetoxy-3-N-acetyl-t-butylaminopropoxy)-5-methylphenyl]-3(2H)-pyridazinone which crystallised from ethanol and had m.p. 140°-144°.

(vii) 6-[2-Acetoxy-3-N-acetyl-t-butylaminopropoxy)-5-methylphenyl]-3(2H)-pyridazinone was treated with phosphorus pentasulphide in a similar manner to the procedure described in Example 2 (iv) to give 6-[2-(2-acetoxy-3-N-acetyl-t-butylaminopropoxy)-5-methylphenyl]-3(2H)-pyridazinethione which was crystallised from ethanol and had 162.5°-164°.

(vii) 6-[2-(2-Acetoxy-3-N-acetyl-t-butylaminopropoxy)-5-methylphenyl]-3(2H)-pyridazinethione was treated with methanolic sodium hydroxide solution in a similar manner to the procedure described in Example 2 (v) to give 6-[2-(2-t-butylamino-3-hydroxypropoxy)-5-methylphenyl]-3(2H)-pyridazinethione which was crystallised from 2-methoxyethanol and had m.p. ca. 130°.

(ix) 6-[2-(2-t-Butylamino-3-hydroxypropoxy)-5-methylphenyl]-3(2H)-pyridazinethione was treated with hydrazine hydrate in a similar manner to the procedure described in Example 2 (vi) to give 3-[2-(2-t-butylamino-3-hydroxypropoxy)-5-methylphenyl]-6-hydrazinopyridazine as an oil which was isolated as the hemisulphate, m.p. 172°-178° C. (Found: C, 54.6; H, 7.1; N, 17.5; S, 3.9% $C_{18}H_{27}N_5O_2 \cdot 0.5H_2SO_4$ requires: C, 54.8; H, 7.2; N, 17.8; S, 4.1%

EXAMPLE 19

6-[2-(3-t-Butylamino-2-hydroxypropoxy)-5-chlorophenyl]-3(2H-pyridazinethione (i) 4-Chlorphenol was reacted with succinic anhydride and aluminium chloride in a similar manner to the procedure described in Example 8 (i) to give 3-(5-chloro-2-hydroxybenzoyl)propionic acid (49%, m.p. 172°-173° C). (Found: M+, 228/230. $C_{10}H_9Cl\ O_4$ requires: M, 228/230).

(ii) 3-(5-Chloro-2-hydroxybenzoyl)propionic acid was esterfied with methanol-hydrogen chloride in a similar manner to the procedure described in Example 1 (i) to give methyl 3-(3-chloro-2-hydroxybenzoyl)propionate (75%).

(iii) Methyl 3-(5-chloro-2-hydroxybenzoyl)propionate was reacted with epibromohydrin in a similar manner to the procedure described in Example 1 (ii) to give methyl 3-[5-chloro-2-(2,3-epoxypropoxy)benzoyl]propionate as an oil (53%).

(iv) Methyl 3-[5-chloro-2-(2,3-epoxypropoxy)benzoyl-propionate was treated with t-butylamine in a similar manner to the procedure described in Example 2 (i) to give methyl 3-[2-(3-t-butylamino-2-hydroxypropoxy)-5-chlorobenzoyl propionate, which was crystallised from ether-light petroleum (90%, m.p. 84°-85° C).

(v) Methyl 3-[2-(3-t-butylamino-2-hydroxypropoxy)-5-chlorobenzoyl]propionate was cyclised with hydrazine hydrate in a similar manner to the procedure described in Example 2(ii) to give 6-[2(3-t-butylamino-2-hydroxypropoxy)-5-chlorophenyl]-4,5-dihydro-3(2H)-pyridazinone.

(vi) 6-[2-(3-t-butylamino-2-hydroxypropoxy)-5-chlorophenyl]-4,5-dihydro-3(2H)-pyridazinone was reacted in a similar manner to the procedure described in Example 2(iii) to give 6-[2-(2-acetoxy-3-N-acetyl-t-butylaminopropoxy)-5-chlorophenyl]-3(2H)-pyridazinone which crystallised from ethanol. (77%, m.p. 136.5°- 138.5° C).

(vii) 6-[2-(2-Acetoxy-3-N-acetyl-t-butylaminopropoxy)-5-chlorophenyl]-3(2H)-pyridazinone was treated with phosphorus pentasulphide in a similar manner to the procedure described in Example 2 (iv) to give 6-[2-(2-acetoxy-3-N-acetyl-t-butylaminopropoxy)-5-chlorophenyl]-3(2H)-pyridazinethione which was crystallised from ethanol. (57%, m.p. 191°-192° C).

(viii) 6-[2-(2-Acetoxy-3-N-acetyl-t-butylaminopropoxy)-5-chlorophenyl]-3-(2H)-pyridazinethione was treated with methanolic sodium hydroxide solution in a similar manner to the procedure described in Example 2 (v) to give 6-[2-(2-t-butylamino-3-hydroxypropoxy)-5-chlorophenyl]-3(2H)-pyridazinethione which was crystallised from ethanol (57%, m.p. 168°-170° C).

EXAMPLE 20

6-[2-(3-t-Butylamino-2-hydroxypropoxy)-5-methoxyphenyl]-3(2H)-pyridazinethione (i) 3-(2-Hydroxy-5-methoxybenzoyl)propionic acid was esterified with methanol-hydrogen chloride, in a similar manner to the procedure described in Example 1

(i), to give methyl 3-(2-hydroxy-5-methoxybenzoyl)-propionate as an oil.

(ii) Methyl 3-(2-hydroxy-5-methoxybenzoyl)propionate was reacted with epibromohydrin in a similar manner to that described in Example 1 (ii) to give methyl 3-[2-(2,3-epoxypropoxy)-5-methoxybenzoyl]propionate which, recrystallised from ether-petroleum ether (b.p. 60°–80°), had m.p. 50° – 51.5° C). (Found: C, 60.91; H, 6.07; $C_{15}H_{18}O_6$ requires: C, 61.21; H, 6.17%).

(iii) Methyl 3-[2-(2,3-epoxypropoxy)-5-methoxybenzoyl]-propionate was reacted with t-butylamine in a similar manner to that described in Example 2 (i) to give methyl 3-[2-(3-t-butylamino-2-hydroxypropoxy)-5-methoxybenzoyl]-propionate, which recrystallised from ether, had m.p. 70° – 72° C. (Found: C, 62.22; H, 8.22; N, 3.65; $C_{19}H_{29}NO_6$ requires: C, 62.10; H, 7.96; N, 3.81%)

(iv) Methyl 3-[2-(3-t-butylamino-2-hydroxypropoxy)-5-methoxybenzoyl]propionate was cyclised with hydrazine hydrate in a similar manner to that described in Example 2 (ii) to give 6-[2-(3-t-butylamino-2-hydroxypropoxy)-5-methoxyphenyl]-4,5-dihydro-3(2H)-pyridazinone (m.p. 127°–128° C). The hydrochloride, crystallised from methanolether, had m.p. 227°–229° C. (Found: C, 56.24; H, 7.24; Cl, 9.06; N, 10.75; $C_{18}H_{27}N_3O_4 \cdot HCl$ requires: C, 56.03; H, 7.31; Cl, 9.19; N, 10.88%)

(v) The title compound was prepared by subjecting 6-[2-(3-t-butylamino-2-hydroxypropoxy)-5-methoxyphenyl]-4,5-dihydro-3(2H)-pyridazinone to a series of reactions similar to those described in Example 2 (iii-v). It had m.p. 187.5° – 189.5° C and formed a hydrochloride, m.p. 219° – 222° C.

EXAMPLE 21

6-[2-(3-(2-Phenylethylamino)-2-hydroxypropoxy)-phenyl]-3(2H)-pyridazinethione

Substitution of 2-phenylethylamine for t-butylamine in the procedure of Example 2 leads to the preparation of the title compound.

EXAMPLE 22

6-[2-(3-t-Butylamino-2-hydroxypropoxy)-4-allyloxyphenyl]-3(2H)-pyridazinethione

Treatment of methyl 3-(2,4-dihydroxybenzoyl)propionate with 1.1 equivalents of allylbromide and potassium carbonate in butan-2-one gives methyl 3-(2-hydroxy-4-allyloxybenzoyl)propionate, and substitution of the latter compound for methyl 3-(2-hydroxybenzoyl)propionate in the general procedure of Example 1 (ii) gives methyl 3-[2-(2,3-epoxypropoxy)-4-allyloxybenzoyl]propionate and treatment of this compound by the general procedure of Example 2 (i - v) gives the title product.

EXAMPLE 23

| Ingredients | Amounts |
| --- | --- |
| 6-[2-(3-t-Butylamino-2-hydroxypropoxy)-phenyl]-3(2H)-pyridazinethione | 75 mg |
| Sucrose | 40 mg |
| Starch | 15 mg |
| Talc | 3 mg |

| Ingredients | Amounts |
| --- | --- |
| -continued | |
| Stearic Acid | 1 mg |

The ingredients are screened, mixed and filled into a hard gelatin capsule.

EXAMPLE 24

| Ingredients | Amounts |
| --- | --- |
| 6-[2-(3-t-Butylamino-2-hydroxypropoxy)-phenyl]-3(2H)-pyridazinethione | 100 mg |
| Lactose | 50 mg |

The ingredients are screened, mixed and filled into a hard gelatin capsule.

We claim:
1. A compound of the formula:

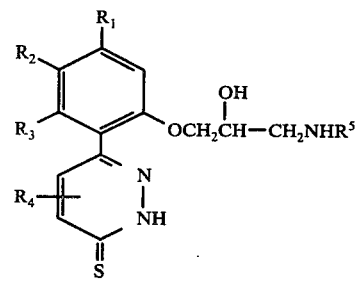

wherein two of the groups $R_1$, $R_2$ and $R_3$ are hydrogen and the third group is hydrogen, lower alkyl, fluoro, chloro, bromo, trifluoromethyl, hydroxy, lower alkoxy, lower alkenyloxy, lower alkoxycarbonyl, cyano, —$CONH_2$, —$CH_2CONH_2$, nitro, amino, lower alkanoylamino, lower alkylamino or di(lower alkyl)amino; $R_4$ is hydrogen or methyl; and $R^5$ is isopropyl, tertiary butyl or 2-phenylethyl.

2. A compound of claim 1 wherein $R_1$, $R_2$ and $R_3$ are all hydrogen.

3. A compound of claim 1 wherein one of $R_1$, $R_2$ and $R_3$ is methyl, fluoro, chloro, methoxy or cyano.

4. A compound of claim 3 wherein $R_3$ is hydrogen.

5. A compound of claim 1 wherein $R_3$ is hydrogen and either $R_1$ or $R_2$ is trifluoromethyl, allyloxy, —$CH_2CONH_2$ or acetamido.

6. A compound of claim 5 wherein either $R_1$ or $R_2$ is —$CH_2CONH_2$ or acetamido.

7. A compound of claim 1 wherein $R_4$ is hydrogen.

8. A compound of claim 1 wherein $R^5$ is isopropyl or tertiary butyl.

9. A compound of claim 1 said compound being 6-[2-(3-t-butylamino-2-hydroxypropoxy)phenyl]3(2H)-pyridazinethione.

10. A compound of claim 1 said compound being 6-[2-(3-t-butylamino-2-hydroxypropoxy)-4-methylphenyl]-3(2H)-pyridazinethione.

11. A compound of claim 1 said compound being 6-[2-(3-t-butylamino-2-hydroxypropoxy)-4-methoxyphenyl]-3(2H)-pyridazinethione.

12. A compound of claim 1 said compound being 6-[4-acetamido-2-(3-t-butylamino-2-hydroxypropoxy)-phenyl]-3(2H)-pyridazinethione.

13. A compound of claim 1 in the S-absolute configuration.

* * * * *